(12) United States Patent
Matsunaga et al.

(10) Patent No.: US 7,550,630 B2
(45) Date of Patent: Jun. 23, 2009

(54) PROCESS FOR PRODUCING N-(BICYCLO[2.2.1]HEPT-5-EN-2-YLMETHYL)-1,1,1-TRIFLUOROMETHANE-SULFONAMIDE

(75) Inventors: Kei Matsunaga, Saitama (JP); Takeo Komata, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 194 days.

(21) Appl. No.: 11/878,592

(22) Filed: Jul. 25, 2007

(65) Prior Publication Data

US 2008/0071113 A1 Mar. 20, 2008

(30) Foreign Application Priority Data

Jul. 26, 2006 (JP) .............................. 2006-203792
Jun. 29, 2007 (JP) .............................. 2007-173216

(51) Int. Cl.
*C07C 303/38* (2006.01)

(52) U.S. Cl. ....................................................... 564/97
(58) Field of Classification Search .................... 564/97
See application file for complete search history.

(56) References Cited

U.S. PATENT DOCUMENTS

| 5,514,493 A | 5/1996 | Waddell et al. |
| 5,723,664 A | 3/1998 | Sakaguchi et al. |
| 5,874,616 A | 2/1999 | Howells et al. |

FOREIGN PATENT DOCUMENTS

| JP | 8-81436 A | 3/1996 |
| JP | 11-209338 A | 8/1999 |
| WO | WO 97/23448 A1 | 7/1997 |

OTHER PUBLICATIONS

Zhurnal Organicheskoi Khimii, Russia, 1995, 31(3), pp. 357-364.
J. Burdon et al. "Fluorinated Sulphonic Acids. Part I. Perfluoromethane, octane, and decane-sulphonic Acids and their Simple Derivatives", Journal of Chemical Society, vol. 6(5), pp. 2574-2578 (Published in 1957).

*Primary Examiner*—Peter G O'Sullivan
(74) *Attorney, Agent, or Firm*—Crowell & Moring LLP

(57) ABSTRACT

A process for producing N-(bicyclo[2.2.1]hept-5-en-2-ylmethyl)-1,1,1-trifluoromethanesulfonamide represented by formula [3]. The process includes the step of reacting trifluoromethanesulfonic anhydride with 1-bicyclo[2.2.1]hept-5-en-2-ylmethanamine in the presence of water and in the presence of a base selected from the group consisting of alkali metal hydroxides, alkaline-earth metal hydroxides and basic salts containing an alkali metal or an alkaline-earth metal.

[3]

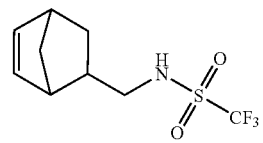

11 Claims, No Drawings

PROCESS FOR PRODUCING N-(BICYCLO[2.2.1]HEPT-5-EN-2-YLMETHYL)-1,1,1-TRIFLUOROMETHANE-SULFONAMIDE

BACKGROUND OF THE INVENTION

The present invention relates to a process for producing N-(bicyclo[2.2.1]hept-5-en-2-ylmethyl)-1,1,1-trifluoromethanesulfonamide represented by formula [3], which is a useful compound as an organic intermediate, such as monomers corresponding to the next generation photoresist.

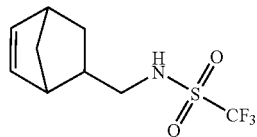
[3]

N-(bicyclo[2.2.1]hept-5-en-2-ylmethyl)-1,1,1-trifluoromethanesulfonamide represented by formula [3] is a useful compound as an organic intermediate, the useful compound being expected to be, for example, a monomer corresponding to the next generation photoresist.

It is disclosed in non-patent publication 1 that N-(bicyclo[2.2.1]hept-5-en-2-ylmethyl)-1,1,1-trifluoromethanesulfonamide can be synthesized by the following process "a" or process "b".

[Process "a"]

It is a process in which trifluoromethanesulfonic anhydride represented by formula [1] is reacted with 1-bicyclo[2.2.1] hept-5-en-2-ylmethaneamine represented by formula [2] in an anhydrous methylene chloride solvent in the presence of triethylamine serving as a base.

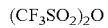
(CF$_3$SO$_2$)$_2$O    [1]

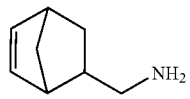
[2]

[Process "b"]

It is a process in which trifluoromethanesulfonic fluoride represented by formula [4] is reacted with 1-bicyclo[2.2.1] hept-5-en-2-ylmethaneamine represented by formula [2] in an anhydrous methylene chloride solvent in the presence of triethylamine serving as a base.

CF$_3$SO$_2$F    [4]

A sulfonamidation reaction in which a sulfonic halide is used as a sulfonation agent is a well-known process in general. With this reaction, a sulfonamide compound can be produced with relatively high selectivity. Other than the above-mentioned process "b" in which trifluoromethanesulfonic fluoride is used as a raw material, there is known an example as follows, though the target compound thereof is different from that of process "b".

(Example of Non-Patent Publication 2)

Trifluoromethanesulfonic chloride represented by formula [5] is used as a sulfonation agent. This is reacted with aniline in an anhydrous ether solvent in the presence of pyridine serving as a base, thereby synthesizing trifluoromethanesulfonic anilide.

CF$_3$SO$_2$Cl    [5]

(Example of Non-Patent Publication 1)

As a sulfonation agent, m-trifluoromethylphenylsulfonic chloride is used. This is reacted with 1-bicyclo[2.2.1]hept-5-en-2-ylmethaneamine represented by formula [2] in an ether solvent in the presence of 20% sodium hydroxide aqueous solution serving as a base, thereby synthesizing N-(m-trifluoromethylphenylsulfonyl)-5-aminomethylbicyclo[2.2.1]hept-2-en. In addition to this, patent publications 1 to 3, etc. are known as reaction examples of forming a [—SO$_2$—NH—] bond by reacting a sulfonic halide containing a trifluoromethyl group with an amine-series compound.

[Non-patent Publication 1] Zhurnal OrganicheskoiKhimii (Russia), (1995), 31 (3), p. 357-64

[Non-patent Publication 2] Journal of Chemical Society, vol. 6 (5), p. 2574-2578 (published in 1957)

[Patent Publication 1] Japanese Patent Application Publication 8-81436

[Patent Publication 2] Japanese Patent Application Publication 11-209338

[Patent Publication 3] International Publication 97/23448 Pamphlet

SUMMARY OF THE INVENTION

As mentioned above, many examples are known as a reaction of forming a [—SO$_2$—NH—] bond by reacting a sulfonic halide with an amine. However, there is a problem that "a halogen addition reaction to an unsaturated bond" occurs as a side reaction, in a sulfonamidation using a sulfonic halide as a raw material. For example, when a sulfonamide compound is synthesized by using trifluoromethanesulfonic chloride as a raw material, N-[(6-chlorobicyclo[2.2.1]hept-5-en-2-yl)methyl]-1,1,1-trifluoromethanesulfonamide (a chlorine adduct) represented by the following formula is produced as a by-product by 2% to 3% (see Referential Example as discussed below).

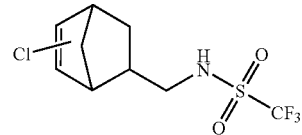

It is not easy to separate this "halogen adduct" from the target product. For example, a rectification using a distillation column of many stages is necessary for the separation by distillation. The distillation yield is also low, and it is not necessarily advantageous for the production in a large-amount scale.

In contrast with this, there are far less examples of synthesizing a sulfonamide by reacting "sulfonic anhydride" with an amine (the above-mentioned [process "a"]). Since there exist two alkyl chains (e.g., CF$_3$ groups) in one molecule of sulfonic anhydride, its unit price is frequently higher as compared with sulfonic halide. The above-mentioned side reaction (addition reaction), however, does not proceed in the case of using sulfonic anhydride. As a result of this, the purification load after the reaction is considerably reduced. Particularly in a case where the required purity of the target product is high, it becomes rather advantageous overall. In particular, contamination of a material used for electronic materials with chlorine is not favorable. Therefore, it is very useful to use "trifluoromethanesulfonic anhydride", which does not produce a chlorine adduct as a by-product, upon producing the target product served for such use.

As mentioned above, the above process "a" is known as a process for producing N-(bicyclo[2.2.1]hept-5-en-2-ylmethyl)-1,1,1-trifluoromethanesulfonamide by using this "sulfonic anhydride" as a raw material. According to this process, there are merits that the target product can be produced with high selectivity and that by-products difficult to be separated are not produced.

However, a main problem of this process is to use a relatively high-price organic base, triethylamine. Furthermore, this base is high in treatment cost, since it must be treated as an organic liquid waste after the reaction. Furthermore, "a triethylamine salt of trifluoromethanesulfonic acid", which is hardly soluble both in water and in organic phase, is precipitated as a by-product with the reaction. Therefore, it is essential to have a step of removing the salt by filtration, thereby causing an excessive load on the post-treatment.

In other words, the process using "trifluoromethanesulfonic anhydride" as a raw material, which is described in non-patent publication 1, is a process useful for producing the target product in a small scale to a medium scale. It is, however, still not sufficient in the production in a large-amount scale. Thus, there has been a demand for a further improvement.

In view of such problems, the present inventors have conducted an eager examination in order to establish a production process of N-(bicyclo[2.2.1]hept-5-en-2-ylmethyl)-1,1,1-trifluoromethanesulfonamide that is suitable for the production in a large-amount scale.

As a result, we have found that the target N-(bicyclo[2.2.1]hept-5-en-2-ylmethyl)-1,1,1-trifluoromethanesulfonamide represented by formula [3] can be produced with high yield by reacting trifluoromethanesulfonic anhydride represented by formula [1], with 1-bicyclo[2.2.1]hept-5-en-2-ylmethaneamine represented by formula [2], in the presence of water and in the presence of a base selected from "a hydroxide of an alkali metal or alkaline-earth metal, or a basic salt containing an alkali metal or alkaline-earth metal", thereby reaching the present invention.

In the present invention, a base selected from "a hydroxide of an alkali metal or alkaline-earth metal, or a basic salt containing an alkali metal or alkaline-earth metal" corresponds to a substance that is generally known as "an inorganic base". Herein, "a basic salt containing an alkali metal or alkaline-earth metal" is a salt of an alkali metal hydroxide or alkaline-earth metal hydroxide with "a weak acid or midrange acid" such as acetic acid, propionic acid, boric acid, phosphoric acid, and carbonic acid. It refers to one showing basicity (it refers to one showing a pH value of not smaller than 8, when an aqueous solution, for example, having a concentration of 0.1 mol·dm$^{-3}$ is prepared). It became possible to greatly reduce the production cost, since it became possible to use such inorganic base.

In the present invention, it is important to make water coexistent in the reaction system. That is, water is made coexistent to have a two-phase system (a heterogeneous system). With this, the target reaction turned out to proceed with high yield even in the case of using "an inorganic base". A trifluoromethanesulfonate, which is produced as a by-product with the reaction, is easily soluble in water. Therefore, the load of the purification treatment after the reaction was greatly reduced.

It is generally known that, when an acid anhydride is brought into contact with water, it is easily decomposed into the corresponding acid (carboxylic acid and sulfonic acid) (see, for example, "Kagaku Daijiten" (Kyoritsu Publishing Co.), Vol. 3, p. 997). Therefore, in the case of using a carboxylic anhydride or sulfonic anhydride as a reaction agent, the reaction is conducted only under an anhydrous condition. The above process "a" is not an exception to this, either.

However, in regard to the synthesis of N-(bicyclo[2.2.1]hept-5-en-2-ylmethyl)-1,1,1-trifluoromethanesulfonamide, it is found that, in the case of using trifluoromethanesulfonic anhydride as the raw material and the above-mentioned "inorganic base" as the base in accordance with the above process "a", the target reaction proceeds with very low yield under an anhydrous condition (see Comparative Example 1).

In view of such condition, the present inventors have tried to make water coexistent in the system and have found that the target reaction unexpectedly proceeds with high yield. That is, it has been found that, even if water is coexistent in the system in the present reaction system, "the decomposition of trifluoromethanesulfonic anhydride by water" does not occur significantly, and the target reaction occurs predominantly. As a result, it became possible to remarkably advantageously produce N-(bicyclo[2.2.1]hept-5-en-2-ylmethyl)-1,1,1-trifluoromethanesulfonamide as compared with the conventional techniques.

The present inventors have found that it proceeds still more preferably by conducting the above reaction in a manner to gradually or continuously add either trifluoromethanesulfonic anhydride represented by formula [1] or water into the reaction system.

Furthermore, the present inventors have found that the above reaction proceeds still more preferably under a coexistence of a non-aqueous organic solvent. Furthermore, it has been found still more preferable to use particular ones in terms of the type of the above "inorganic base", the amount of water, the type and the amount of the non-aqueous organic solvent, and the like, thereby reaching the completion of the present invention.

An aspect of the present invention resides in a process for producing N-(bicyclo[2.2.1]hept-5-en-2-ylmethyl)-1,1,1-trifluoromethanesulfonamide represented by formula [3] which process comprises the step of reacting trifluoromethanesulfonic anhydride represented by the formula [1] with 1-bicyclo[2.2.1]hept-5-en-2-ylmethanamine represented by the formula [2] in the presence of water and in the presence of a base selected from the group consisting of alkali metal hydroxides, alkaline-earth metal hydroxides and basic salts containing an alkali metal or an alkaline-earth metal.

[1]

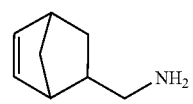

[2]

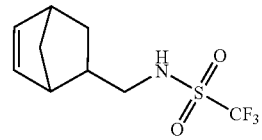

[3]

Another aspect of the present invention resides in a process for producing N-(bicyclo[2.2.1]hept-5-en-2-ylmethyl)-1,1, 1-trifluoromethanesulfonamide represented by the formula [3] which process comprises the sequential steps of: (a) charging a reactor with (i) 1-bicyclo[2.2.1]hept-5-en-2-ylmethanamine represented by the formula [2], (ii) 0.2-100 g of water per gram of the 1-bicyclo[2.2.1]hept-5-en-2-ylmethanamine, (iii) 0.5-100 g of a nonaqueous organic solvent per gram of the 1-bicyclo[2.2.1]hept-5-en-2-ylmethanamine, and (iv) a base that is at least one selected from the group consisting of lithium hydroxide, sodium hydroxide, potassium hydroxide, magnesium hydroxide, calcium hydroxide, barium hydroxide, potassium carbonate, sodium carbonate, sodium hydrogencarbonate, sodium acetate, potassium acetate, disodium hydrogenphosphate, and dipotassium hydrogenphosphate; and (b) intermittently or continuously introducing trifluoromethanesulfonic anhydride represented by the formula [1] into the reactor at a temperature of −10 to 50° C., thereby reacting the trifluoromethanesulfonic anhydride with the 1-bicyclo[2.2.1]hept-5-en-2-ylmethanamine.

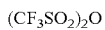  [1]

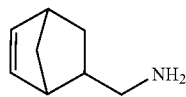  [2]

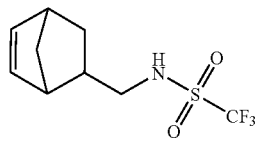  [3]

According to the present invention, there is provided a process for producing N-(bicyclo[2.2.1]hept-5-en-2-ylmethyl)-1,1,1-trifluoromethanesulfonamide, characterized in trifluoromethanesulfonic anhydride represented by formula [1] is reacted with 1-bicyclo[2.2.1]hept-5-en-2-ylmethaneamine represented by formula [2] in the presence of an inorganic base and in a heterogeneous system in which water and a non-aqueous organic solvent are mixed. According to the present invention, it is possible to produce the target product with high yield from raw materials of low prices. Additionally, since it is possible to use "an inorganic base", the operational load after the reaction, such as liquid waste treatment, is also reduced. It is useful for producing the target compound in a large-amount scale. According to the process of the present invention, it is not necessary to use halogenated hydrocarbons and the like, such as methylene chloride, which are hazardous substances. It is possible to delete a step of removing the salt by filtration. This also makes the operation easy. Therefore, it is a particularly useful process to produce the target product in an industrial scale and with high yield.

DETAILED DESCRIPTION OF THE INVENTION

In the following, the present invention will be explained in more detail. The present invention is achieved by reacting a trifluoromethanesulfonic anhydride represented by formula [1] with 1-bicyclo[2.2.1]hept-5-en-2-ylmethaneamine represented by formula [2], in the presence of water and in the presence of a base selected from "a hydroxide of an alkali metal or alkaline-earth metal, or a basic salt containing an alkali metal or alkaline-earth metal". Although its reaction conditions will be described in the following, they do not interfere with the changes of the reaction conditions to the extent that a skilled person can easily adjust them.

(Reaction Mode)

The process of the present invention is easily and advantageously conducted with a batch-type reaction apparatus.

It is possible to minimize the contact between trifluoromethanesulfonic anhydride and water by conducting a manner to gradually add or continuously add either trifluoromethanesulfonic anhydride or water into the reaction system. This is preferable since it is possible to suppress the decomposition reaction into trifluoromethanesulfonic acid, which is an unnecessary side reaction. As mentioned above, the production of the target compound N-(bicyclo[2.2.1]hept-5-en-2-ylmethyl)-1,1,1-trifluoromethanesulfonamide antecedes the decomposition reaction into trifluoromethanesulfonic acid in the reaction system of the present invention. Therefore, it is possible to obtain the target product even if such gradual or continuous addition manner is not taken. However, it is possible to improve yield of the target product and it also becomes easy to control the reaction by taking the gradual or continuous addition manner. Therefore, it is particularly preferable in the present invention to gradually add or continuously add either trifluoromethanesulfonic anhydride or water into the reaction system and to adjust the addition rate while measuring the progress condition of the reaction and the temperature of the reaction system. In particular, a method of gradually or continuously adding trifluoromethanesulfonic anhydride is preferable.

(Mixing Ratio of Raw Materials)

There is no particular limitation in the mixing ratio of trifluoromethanesulfonic anhydride represented by formula [1] to 1-bicyclo[2.2.1]hept-5-en-2-ylmethaneamine represented by formula [2], which are the starting raw materials used in the present invention. It is, however, a reaction in a molar ratio of 1:1. Therefore, it is preferable to mix both at around equimolar ratio (1:1). Specifically, trifluoromethanesulfonic anhydride is in generally 0.5 moles to 2 moles, preferably 0.9 moles to 1.5 moles, more preferably 1 mole to 1.2 moles, relative to 1 mol of 1-bicyclo[2.2.1]hept-5-en-2-ylmethaneamine. If it is less than 0.5 moles, 1-bicyclo[2.2.1]hept-5-en-2-ylmethaneamine that is not involved in the reaction increases. With this, it is economically disadvantageous. Furthermore, the coloring may occur after the reaction, and it may cause a load on purification. If it exceeds 2 moles, trifluoromethanesulfonic anhydride that is not involved in the reaction increases. This is economically not preferable due to disposal work.

(Regarding Base)

As the base usable in the present invention, it is possible to cite "a hydroxide of an alkali metal or alkaline-earth metal, or a basic salt containing an alkali metal or alkaline-earth metal" such as alkali metal hydroxides and alkaline-earth metal hydroxides, such as lithium hydroxide, sodium hydroxide, potassium hydroxide, magnesium hydroxide, calcium hydroxide and barium hydroxide, lithium carbonate, potassium carbonate, sodium carbonate, lithium hydrogencarbonate, sodium hydrogencarbonate, sodium acetate, potassium acetate, disodium hydrogenphosphate, and dipotassium hydrogenphosphate. Of these, sodium carbonate, potassium carbonate, sodium hydroxide, and potassium hydroxide are particularly preferable, due to their economy, handling easiness, high reactivity as the base, etc.

The amount of the base used in the present reaction is, in case that it is a monovalent base, in 0.2 moles to 2 moles, preferably 0.5 moles to 1.5 moles, more preferably 0.9 moles to 1.2 moles, relative to 1 mol of 1-bicyclo[2.2.1]hept-5-en-2-ylmethaneamine of the substrate. If the amount of the base is less than 0.2 moles relative to 1 mol of 1-bicyclo[2.2.1]hept-5-en-2-ylmethaneamine of the substrate, both of selectivity of the reaction and yield of the target product lower. If it exceeds 2 moles, it is economically not preferable due to the increase of the base that is not involved in the reaction. These quantitative relationships are inversely proportional to the valence of the base. For example, it is a half of this in the case of a bivalent base.

(Regarding the Amount of Water)

In the present invention, it is necessary to make water coexistent in the reaction system in order to achieve the increase of the reactivity. By making water coexistent, a trifluoromethanesulfonate that precipitates with the reaction is dissolved in the aqueous phase. Therefore, in contrast with Non-patent Publication 1, it is possible to avoid "precipitation of a hardly soluble salt", and operability is remarkably improved.

The amount of water to be made coexistent is in normally 0.2 g to 100 g (20 wt % to 10,000 wt %), preferably 1 g to 10 g (100 wt % to 1,000 wt %), more preferably 2 g to 6 g (200 wt % to 600 wt %) relative to 1 g of 1-bicyclo[2.2.1]hept-5-en-2-ylmethaneamine. If the amount of water to be coexistent is less than 0.2 g (20 wt %) relative to 1 g of 1-bicyclo[2.2.1]hept-5-en-2-ylmethaneamine, the degree of yield improvement is small, and it is difficult to obtain the advantageous effect of specially adding water. In contrast with this, if the amount of water is in 1 g (100 wt %) or greater, more preferably 1.5 g (150 wt %) or greater, more preferably 2 g (200 wt %) or greater, it is possible to dissolve a sufficient amount of the inorganic base used in the present invention and to secure a high reactivity. Furthermore, it is possible to more securely dissolve trifluoromethanesulfonate that is produced as a by-product with the reaction. It is greatly advantageous to use such an excessive amount of water, particularly in the case of conducting the reaction in a large-amount scale. Therefore, it is still more preferable that the amount of water is in 1.5 g to 6 g, particularly 2 g to 6 g (200 wt % to 600 wt %) to conduct the present invention. The present invention is characterized in that, even such a large excess of water is made coexistent in the system, the reaction of the trifluoromethanesulfonic anhydride with water does not occur significantly, and the reaction with 1-bicyclo[2.2.1]hept-5-en-2-ylmethaneamine represented by formula [2] is greatly accelerated.

On the other hand, if the amount of water exceeds 100 g, it is economically not preferable from the viewpoint of productivity.

(Regarding Non-Aqueous Organic Solvent)

In the present reaction, it is preferable to make a non-aqueous organic solvent further coexistent in the system for the purpose of improving yield and facilitating a separation between the produced target product and a trifluoromethanesulfonate aqueous solution produced as a by-product.

The type of the non-aqueous organic solvent usable is not particularly limited. It is possible to use: saturated hydrocarbon compounds such as pentane, hexane and heptane; aromatic compounds such as benzene, toluene, xylene and mesitylene; ether compounds such as diethyl ether, methyl-t-butyl ether, diisopropyl ether, and tetrahydrofuran; halogenated hydrocarbon compounds such as methylene chloride, chloroform, and carbon tetrachloride. These may be used singly, or a plurality of solvents may be used together. Furthermore, as mentioned above, methylene chloride was used in Non-patent Publication 1. In the present invention, however, there is an advantage that the reaction proceeds well even if such halogenated hydrocarbon is not used. To further use the advantage, it is still more preferable in the present invention to use toluene, xylene, pentane, hexane, diisopropyl ether and the like, which are less in environmental load, as compared with halogenated hydrocarbons, benzene and the like.

In the case of using a non-aqueous organic solvent in the present reaction, its amount is normally 0.5 g to 100 g, preferably 1 g to 10 g, more preferably 2 g to 5 g, relative to 1 g of 1-bicyclo[2.2.1]hept-5-en-2-ylmethaneamine. If the amount of the solvent is 1 g, particularly, 2 g or greater, a good two-phase system is formed by an aqueous phase in which an inorganic base is dissolved and an organic phase in which the reactants are dissolved. This is good from the viewpoint of yield of the target product. On the other hand, if the amount of the solvent is less than 0.5 g relative to 1 g of 1-bicyclo[2.2.1]hept-5-en-2-ylmethaneamine, an operability problem such as difficulty of separating the two layers after the reaction, may occur. If it exceeds 100 g, it is economically not preferable from the viewpoint of productivity.

To conduct the present invention, it is a preferable combination that water is in 1 g to 10 g and the non-aqueous organic solvent is in 1 to 10 g, relative to 1 g of 1-bicyclo[2.2.1]hept-5-en-2-ylmethaneamine. It is a particularly preferable combination that water is in 2 to 6 g and the non-aqueous organic solvent is in 2 to 5 g.

(Regarding Temperature)

The reaction temperature upon conducting the present invention is normally −20 to 100° C., preferably −15 to 70° C., more preferably −10 to 50° C. If it is lower than −20° C., operability lowers since water in the reaction system solidifies in some cases. If it exceeds 100° C., the product decomposition and the like may occur. Therefore, it is not preferable.

(Regarding the Reactor)

The reactor for conducting the reaction of the present invention is not particularly limited. Both of the closed system and the open system can be used. As the material, one lined with tetrafluoroethylene resin, chlorotrifluoroethylene resin, vinylidene fluoride resin, PFA resin, glass or the like, a glass container, or one made of stainless steel is preferable.

Although the process for conducting the present invention is not limited, one example of desirable embodiments is described in detail. A reactor proof against the reaction conditions is charged with a base, a solvent, and 1-bicyclo[2.2.1]hept-5-en-2-ylmethaneamine serving as the raw material. While controlling the temperature from outside, trifluoromethanesulfonic anhydride is added and then stirred. It is preferable to confirm that the reaction has terminated by monitoring the consumption of the raw material by sampling or the like.

(Regarding Purification Method)

N-(bicyclo[2.2.1]hept-5-en-2-ylmethyl)-1,1,1-trifluoromethanesulfonamide represented by formula [3] and produced by the process of the present invention is purified by applying a known method.

After conducting the reaction of the present invention, the target product N-(bicyclo[2.2.1]hept-5-en-2-ylmethyl)-1,1,1-trifluoromethanesulfonamide exists in the organic phase (a phase formed of the unreacted raw materials, the non-aqueous organic solvent and the like), and trifluoromethanesulfonate produced as a by-product exists in the aqueous phase. Therefore, it is possible to easily remove the trifluoromethanesulfonate to the outside of the system by subjecting the reaction liquid to a two-layer separation. Then, it is washed with water, followed by distilling the solvent off, thereby obtaining a crude organic matter. The obtained crude organic matter does not contain by-products that are difficult in separation. Therefore, it is possible to easily obtain the N-(bicyclo[2.2.1]hept-5-en-2-ylmethyl)-1,1,1-trifluoromethanesulfonamide of high purity by conducting a purification such as column chromatography, distillation or the like.

The present invention is a process for producing N-(bicyclo[2.2.1]hept-5-en-2-ylmethyl)-1,1,1-trifluoromethanesulfonamide represented by formula [3]. The process comprises the sequential steps of: charging a reactor with (i) 1-bicyclo[2.2.1]hept-5-en-2-ylmethaneamine represented by formula [2], (ii) 0.2-100 g of water per gram of the 1-bicyclo[2.2.1]hept-5-en-2-ylmethanamine, (iii) 0.5-100 g of a nonaqueous organic solvent per gram of the 1-bicyclo[2.2.1]hept-5-en-2-ylmethanamine, and (iv) a base that is at least one selected from the group consisting of lithium hydroxide, sodium hydroxide, potassium hydroxide, magnesium hydroxide, calcium hydroxide, barium hydroxide, potassium carbonate, sodium carbonate, sodium hydrogencarbonate, sodium acetate, potassium acetate, disodium hydrogenphosphate, and dipotassium hydrogenphosphate; and intermittently or continuously introducing trifluoromethane-sulfonic anhydride represented by formula [1] into the reactor at a temperature of −10 to 50° C., thereby reacting the trifluoromethanesulfonic anhydride with the 1-bicyclo[2.2.1]hept-5-en-2-ylmethanamine. This process allows to operationally advantageously produce N-(bicyclo[2.2.1]hept-5-en-2-ylmethyl)-1,1,1-trifluoromethanesulfonamide with particularly high yield, which is the most preferable embodiment.

A particularly superior example of them is an embodiment in which the reactor is previously charged with a reaction reagent other than trifluoromethanesulfonic anhydride, in which the reaction is conducted by gradually or continuously introducing the trifluoromethanesulfonic anhydride thereto. At the reaction, 2 to 6 g of water and 2 to 5 g of the nonaqueous organic solvent are made coexistent per gram of 1-bicyclo[2.2.1]hept-5-en-2-ylmethaneamine at a temperature of −10 to 50° C.

In the reaction, an isomer mixture can be used as the raw material 1-bicyclo[2.2.1]hept-5-en-2-ylmethaneamine. In this case, a reaction product is obtained as a mixture of the corresponding N-(bicyclo[2.2.1]hept-5-en-2-ylmethyl)-1,1,1-trifluoromethanesulfonamide, which comes to a mixture of two varieties of isomers when taking "endo-" and "exo-" of norbornene into account. It is preferable to be in accordance with a means such as column chromatography in a case where only one of these isomers is isolated.

EXAMPLES

Although the present invention will be described in detail by examples in the following, it is not limited to these embodiments. Herein, "%" of the composition analysis value represents "areal %" of an organic component except the solvent component, the "areal %" being obtained by sampling a part of the reaction mixture and by measuring it by gas chromatography. As a result of measuring the ratio of isomers of 1-bicyclo[2.2.1]hept-5-en-2-ylmethaneamine used in the reaction, by gas chromatography, "endo-"1-bicyclo[2.2.1]hept-5-en-2-ylmethaneamine was 82% while "exo-"1-bicyclo[2.2.1]hept-5-en-2-ylmethaneamine was 18%.

Example 1

A 1 L four-necked flask equipped with a dropping funnel and a stirring apparatus was charged with 100 g of heptane, 17.9 g (0.45 moles) of sodium hydroxide, 200 g (11.1 moles) of water, and 50 g (0.41 moles) of 1-bicyclo[2.2.1]hept-5-en-2-ylmethaneamine, followed by stirring. When the inside temperature became not higher than 10° C. by an outside cooling apparatus, 114 g (0.41 moles) of trifluoromethanesulfonic anhydride was added from the dropping funnel in over 1 hr. After the termination of the dropping, stirring was conducted for 1 hr at an inside temperature of 20° C. Then, the composition was measured by gas chromatography. With this, an isomer mixture of the target N-(bicyclo[2.2.1]hept-5-en-2-ylmethyl)-1,1,1-trifluoromethanesulfonamide was in 99.5% in total. In addition to this, 1-bicyclo[2.2.1]hept-5-en-2-ylmethaneamine of the raw material was detected by 0.5%. The reaction liquid was separated into two layers with a separatory funnel. Then, the organic layer was washed with 100 ml of 5% sulfuric acid aqueous solution, followed by washing two times with 100 ml of water. The solvent was distilled out of the obtained solution, thereby obtaining 92.1 g of a crude organic matter. This crude organic matter was subjected to vacuum distillation (13 Pa) using a simple distillation column whose theoretical plate number is 2 to 3, thereby obtaining a fraction of 120 to 130° C. With this, 88.0 g of an isomer mixture of N-(bicyclo[2.2.1]hept-5-en-2-ylmethyl)-1,1,1-trifluoromethanesulfonamide was obtained. When the composition was measured by gas chromatography, the target product isomer mixture of "endo-"N-(bicyclo[2.2.1]hept-5-en-2-ylmethyl)-1,1,1-trifluoromethanesulfonamide and "exo-"N-(bicyclo[2.2.1]hept-5-en-2-ylmethyl)-1,1,1-trifluoromethanesulfonamide was in 99.9% in total. 1-bicyclo[2.2.1]hept-5-en-2-ylmethaneamine of the raw material was in 0.1%. Yield was 85%.

Example 2

A 1 L four-necked flask equipped with a dropping funnel and a stirring apparatus was charged with 100 g of heptane, 17.9 g (0.45 moles) of sodium hydroxide, 200 g of water, and 50 g (0.41 moles) of 1-bicyclo[2.2.1]hept-5-en-2-ylmethaneamine, followed by stirring. When the inside temperature became not higher than 10° C. by an outside cooling apparatus, 114 g (0.41 moles) of trifluoromethanesulfonic anhydride was added from the dropping funnel in over 1 hr. After the termination of the dropping, stirring was conducted for 1 hr at an inside temperature of 50° C. Then, the composition was measured by gas chromatography. With this, an isomer mixture of the target N-(bicyclo[2.2.1]hept-5-en-2-ylmethyl)-1,1,1-trifluoromethanesulfonamide was in 99.8% in total. In addition to this, 1-bicyclo[2.2.1]hept-5-en-2-ylmethaneamine of the raw material was detected by 0.2%. The reaction liquid was separated into two layers with a separatory funnel. Then, the organic layer was washed with 100 ml of 5% sulfuric acid aqueous solution, followed by washing two times with 100 ml of water. The solvent was distilled out of the obtained solution, thereby obtaining 95.6 g of a crude organic matter. This crude organic matter was subjected to vacuum distillation (13 Pa) using a simple distillation column whose theoretical plate number is 2 to 3, thereby obtaining a fraction of 120 to 130° C. With this, 91.3 g of an isomer mixture of N-(bicyclo[2.2.1]hept-5-en-2-ylmethyl)-1,1,1-trifluoromethanesulfonamide was obtained. When the composition was measured by gas chromatography, the target product isomer mixture of "endo-"N-(bicyclo[2.2.1]hept-5-en-2-ylmethyl)-1,1,1-trifluoromethanesulfonamide and "exo-"N-(bicyclo[2.2.1]hept-5-en-2-ylmethyl)-1,1,1- trifluoromethanesulfonamide was in 99.8% in total. The others were in 0.2%. Yield was 88%.

Example 3

A 1 L four-necked flask equipped with a dropping funnel and a stirring apparatus was charged with 200 g of toluene, 17.9 g (0.45 moles) of sodium hydroxide, 200 g of water, and 50 g (0.41 moles) of 1-bicyclo[2.2.1]hept-5-en-2-ylmethaneamine, followed by stirring. When the inside temperature became not higher than 10° C. by an outside cooling apparatus, 114 g (0.41 moles) of trifluoromethanesulfonic anhydride was added from the dropping funnel in over 1 hr. After the termination of the dropping, stirring was conducted for 1 hr at an inside temperature of 20° C. Then, the composition was measured by gas chromatography. With this, an isomer mixture of the target N-(bicyclo[2.2.1]hept-5-en-2-ylmethyl)-1,1,1-trifluoromethanesulfonamide was in 98.2% in total. The others were detected by 1.8%. The reaction liquid was separated into two layers with a separatory funnel. Then, the organic layer was washed with 100 ml of 5% sulfuric acid aqueous solution, followed by washing two times with 100 ml of water. The solvent was distilled out of the obtained solution, thereby obtaining 94.9 g of a crude organic matter. This crude organic matter was subjected to vacuum distillation (13 Pa) using a simple distillation column whose theoretical plate number is 2 to 3, thereby obtaining a fraction of 120 to 130° C. With this, 91.8 g of an isomer mixture of N-(bicyclo[2.2.1]hept-5-en-2-ylmethyl)-1,1,1-trifluoromethanesulfonamide was obtained. When the composition was measured by gas chromatography, the target product isomer mixture of "endo-"N-(bicyclo[2.2.1]hept-5-en-2-ylmethyl)-1,1,1-trifluoromethanesulfonamide and "exo-"N-(bicyclo[2.2.1]hept-5-en-2-ylmethyl)-1,1,1-trifluoromethanesulfonamide was in 98.8% in total. The others were in 1.2%. Yield was 87%.

Example 4

A 1 L four-necked flask equipped with a dropping funnel and a stirring apparatus was charged with 100 g of heptane, 16.6 g (0.22 moles) of calcium hydroxide, 200 g of water, and 50 g (0.41 moles) of 1-bicyclo[2.2.1]hept-5-en-2-ylmethaneamine, followed by stirring. When the inside temperature became not higher than 10° C. by an outside cooling apparatus, 114 g (0.41 moles) of trifluoromethanesulfonic anhydride was added from the dropping funnel in over 1 hr. After the termination of the dropping, stirring was conducted for 1 hr at an inside temperature of 20° C. After a lapse of 1 hr, the composition was measured by gas chromatography. With this, an isomer mixture of the target N-(bicyclo[2.2.1]hept-5-en-2-ylmethyl)-1,1,1-trifluoromethanesulfonamide was in 99.5% in total. The others were detected by 0.5%. The reaction liquid was separated into two layers with a separatory funnel. Then, the organic layer was washed with 100 ml of 5% sulfuric acid aqueous solution, followed by washing two times with 100 ml of water. The solvent was distilled out of the obtained solution, thereby obtaining 91.5 g of a crude organic matter. This crude organic matter was subjected to vacuum distillation (13 Pa) using a simple distillation column whose theoretical plate number is 2 to 3, thereby obtaining a fraction of 120 to 130° C. With this, 87.8 g of an isomer mixture of N-(bicyclo[2.2.1]hept-5-en-2-ylmethyl)-1,1,1-trifluoromethanesulfonamide was obtained. When the composition was measured by gas chromatography, the target product isomer mixture of "endo-"N-(bicyclo[2.2.1]hept-5-en-2-ylmethyl)-1,1,1-trifluoromethanesulfonamide and "exo-"N-(bicyclo[2.2.1]hept-5-en-2-ylmethyl)-1,1,1-trifluoromethanesulfonamide was in 99.7% in total. The others were in 0.3%. Yield was 85%.

Examples 5 to 10

Synthesis of N-(bicyclo[2.2.1]hept-5-en-2-ylmethyl)-1,1,1-trifluoromethanesulfonamide was conducted under the same conditions as those of Example 1, except for those particularly shown in Table 1.

Comparative Example 1

A 1 L four-necked flask equipped with a dropping funnel and a stirring apparatus was charged with 400 g of diisopropyl ether, 61.7 g (0.45 moles) of potassium carbonate, 100 g (0.81 moles) of 1-bicyclo[2.2.1]hept-5-en-2-ylmethaneamine, followed by stirring. When the inside temperature became not higher than 10° C. by an outside cooling apparatus, 240 g (0.81 moles) of trifluoromethanesulfonic anhydride was added from the dropping funnel in over 1 hr. After the termination of the dropping, stirring was conducted for 1 hr at an inside temperature of 20° C. Then, the composition was measured by gas chromatography. With this, an isomer mixture of the target N-(bicyclo[2.2.1]hept-5-en-2-ylmethyl)-1,1,1-trifluoromethanesulfonamide was in 99.9% in total. The others were detected by 0.1%. The generated salt was removed by filtration, thereby obtaining filtrate. The filtrate was washed with 200 ml of 5% sodium hydrogencarbonate aqueous solution, followed by washing three times with 200 ml of water. The solvent was distilled out of the obtained solution, thereby obtaining 96.5 g of a crude organic matter. This crude organic matter was subjected to vacuum distillation (13 Pa) using a distillation column whose theoretical plate number is 25, thereby obtaining a fraction of 120 to 130° C. With this, 88.6 g of an isomer mixture of N-(bicyclo[2.2.1]hept-5-en-2-ylmethyl)-1,1,1-trifluoromethanesulfonamide was obtained. When the composition was measured by gas chromatography, the target product isomer mixture of "endo-"N-(bicyclo[2.2.1]hept-5-en-2-ylmethyl)-1,1,1-trifluoromethanesulfonamide and "exo-"N-(bicyclo[2.2.1]hept-5-en-2-ylmethyl)-1,1,1-trifluoromethanesulfonamide was in 99.9% in total. The others were in 0.1%. Yield was 43%.

Results of Examples 1 to 10 and Comparative Example 1 are shown in Table 1.

TABLE 1

| Sample | Water | Non-aqueous Organic Solvent | Base | Reaction Temperature | Isolation Yield |
|---|---|---|---|---|---|
| Example 1 | 400% | Heptane (200%) | NaOH 1.1 equivalents | 20° C. | 85.0% |
| Example 2 | 400% | Heptane (200%) | NaOH 1.1 equivalents | 50° C. | 88.0% |
| Example 3 | 400% | Toluene (400%) | NaOH 1.1 equivalents | 20° C. | 87.0% |
| Example 4 | 400% | Heptane (200%) | Ca(OH)$_2$ 1.1 equivalents | 20° C. | 85.0% |
| Example 5 | 200% | Heptane (400%) | NaOH 1.1 equivalents | 20° C. | 83.8% |
| Example 6 | 50% | Heptane (550%) | NaOH 1.1 equivalents | 20° C. | 84.0% |
| Example 7 | 25% | Heptane (575%) | NaOH 1.1 equivalents | 20° C. | 70.1% |
| Example 8 | 400% | Heptane (200%) | K$_2$CO$_3$ 1.1 equivalents | 20° C. | 83.0% |
| Example 9 | 200% | Heptane (400%) | K$_2$CO$_3$ 1.1 equivalents | 20° C. | 84.0% |

TABLE 1-continued

| Sample | Water | Non-aqueous Organic Solvent | Base | Reaction Temperature | Isolation Yield |
|---|---|---|---|---|---|
| Example 10 | 400% | Heptane (200%) | Ba(OH)$_2$•8H$_2$O 1.1 equivalents | 20° C. | 82.1% |
| Comparative Example 1 | None | Diisopropyl Ether (400%) | K$_2$CO$_3$ 1.1 equivalents | 20° C. | 43.0% |

Note:
Water and nonaqueous organic solvent are indicated with an amount relative to the amount of 1-bicyclo[2.2.1]hept-5-en-2-ylmethaneamine taken as 100% by weight Note:
The amount of base is indicated with an equivalent relative to 1-bicyclo[2.2.1]hept-5-en-2-ylmethaneamine whose amount is taken as 1 equivalent (0.5 moles of bivalent base is 1 equivalent)

Note:
The reaction temperature is a temperature fixed during the stirring operation conducted after the termination of the initial dropping As above, there was used in any of Examples 1 to 10 an inorganic base light in load of liquid waste treatment and low in cost, thereby obtaining the target product with remarkably high yield as compared with Comparative Example 1. Furthermore, the target product obtained in Examples 1 to 10 was equal in purity to the following Referential Example 1, even though the distillation conducted after the termination of the reaction was a simple distillation whose theoretical plate number is 2 to 3.

Of Examples 1 to 10, Examples 7 and 6 in which an amount of water was relatively small were excellent in proceeding of the reaction itself. However, a metal salt of trifluoromethanesulfonic acid was precipitated to form slurry, as the reaction proceeded. In contrast to this, in the other Examples (having an amount of water of 200 wt % or more) the precipitation of the slurry was suppressed, so that a further smooth reactivity was observed. As has been discussed, the use of an excessive amount of water has an effect of reducing a load such as stirring, particularly in a case where the target product is produced in a large-amount scale, so as to be found to be high in superiority.

Additionally, it is found from Comparative Example 1 that yield of the target product stays on extremely small value when the inorganic base is used as base under an anhydrous condition in a system using trifluoromethanesulfonic anhydride.

Referential Example 1

A 1 L four-necked flask equipped with a dropping funnel and a stirring apparatus was charged with 300 g of diisopropyl ether, 86.3 g (0.85 moles) of triethylamine, and 100 g (0.81 moles) of 1-bicyclo[2.2.1]hept-5-en-2-ylmethaneamine, followed by stirring. When the inside temperature became not higher than 10° C. by an outside cooling apparatus, 137 g (0.81 moles) of trifluoromethanesulfonic chloride was added from the dropping funnel in over 1 hr. After the termination of the dropping, stirring was conducted for 1 hr at an inside temperature of 20° C. Then, the composition was measured by gas chromatography. With this, an isomer mixture of the target N-(bicyclo[2.2.1]hept-5-en-2-ylmethyl)-1,1,1-trifluoromethanesulfonamide was in 97.3% in total. Additionally, N-[(6-chlorobicyclo[2.2.1]hept-5-en-2-yl)methyl]-1,1,1-trifluoromethanesulfonamide (a chlorine adduct) produced as a by-product was 2.5%. The others were detected by 0.2%. The reaction liquid was separated into two layers with a separatory funnel. Then, the organic layer was washed with 100 ml of 5% sulfuric acid aqueous solution, followed by washing two times with 100 ml of water. The solvent was distilled out of the obtained solution, thereby obtaining 167.3 g of a crude organic matter. This crude organic matter was subjected to vacuum distillation (13 Pa) using a distillation column whose theoretical plate number is 25, thereby obtaining a fraction of 120 to 130° C. With this, 160.1 g of an isomer mixture of N-(bicyclo[2.2.1]hept-5-en-2-ylmethyl)-1,1,1-trifluoromethanesulfonamide was obtained. When the composition was measured by gas chromatography, the target product isomer mixture of "endo-"N-(bicyclo[2.2.1]hept-5-en-2-ylmethyl)-1,1,1-trifluoromethanesulfonamide and "exo-"N-(bicyclo[2.2.1]hept-5-en-2-ylmethyl)-1,1,1-trifluoromethanesulfonamide was in 99.2% in total. The chloride adduct N-[(6-chlorobicyclo[2.2.1]hept-5-en-2-yl)methyl]-1,1,1-trifluoromethanesulfonamide was 0.6%. The others were in 0.2%. Yield was 75%.

As discussed above, Referential Example 1 needed a distillation column whose theoretical plate number is high in order to remove the chloride adduct. This brings about a slight reduction of yield of the isolated target product, as compared with Examples (except for Example 7).

Referential Example 2

The reaction between trifluoromethanesulfonic anhydride represented by formula [1] and 1-bicyclo[2.2.1]hept-5-en-2-ylmethaneamine represented by formula [2] was conducted under the same conditions and operation as those of Example 1. The solvent was anhydrous methylene chloride while the base was triethylamine, according to non-patent publication 1. As a result of this, yield of the isolated target product was in 79%.

The entire contents of Japanese Patent Applications P2006-203792 (filed Jul. 26, 2006) and P2007-173216 (filed Jun. 29, 2007) are incorporated herein by reference.

Although the invention has been described above by reference to certain embodiments and examples of the invention, the invention is not limited to the embodiments and examples described above. Modifications and variations of the embodiments and examples described above will occur to those skilled in the art, in light of the above teachings. The scope of the invention is defined with reference to the following claims.

What is claimed is:

1. A process for producing N-(bicyclo[2.2.1]hept-5-en-2-ylmethyl)-1,1,1-trifluoromethanesulfonamide represented by formula [3], comprising the step of:

reacting trifluoromethanesulfonic anhydride represented by formula [1] with 1-bicyclo[2.2.1]hept-5-en-2-ylmethanamine represented by formula [2] in the presence of water and in the presence of a base selected from the group consisting of alkali metal hydroxides, alkaline-earth metal hydroxides and basic salts containing an alkali metal or an alkaline-earth metal (CF$_3$SO$_2$)$_2$O     [1]

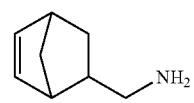

[2]

-continued

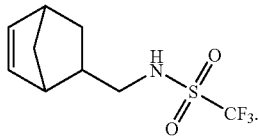
[3]

2. A process as claimed in claim 1, wherein the reacting is conducted by intermittently or continuously adding one of the trifluoromethanesulfonic anhydride represented by formula [1] and the water into a reaction system of the reacting.

3. A process as claimed in claim 1, wherein the reacting is conducted in the presence of a nonaqueous organic solvent.

4. A process as claimed in claim 1, wherein the base is at least one selected from the group consisting of lithium hydroxide, sodium hydroxide, potassium hydroxide, magnesium hydroxide, calcium hydroxide, barium hydroxide, potassium carbonate, sodium carbonate, sodium hydrogencarbonate, sodium acetate, potassium acetate, disodium hydrogenphosphate, and dipotassium hydrogenphosphate.

5. A process as claimed in claim 1, wherein the base is at least one selected from the group consisting of sodium carbonate, potassium carbonate, sodium hydroxide, and potassium hydroxide.

6. A process as claimed in claim 3, wherein the nonaqueous organic solvent is at least one selected from the group consisting of pentane, hexane, heptane, benzene, toluene, xylene, mesitylene, diethyl ether, methyl-t-butyl ether, diisopropyl ether, tetrahydrofuran, methylene chloride, chloroform, and carbon tetrachloride.

7. A process as claimed in claim 1, wherein the water is in an amount of 0.2-100 g per gram of the 1-bicyclo[2.2.1]hept-5-en-2-ylmethanamine.

8. A process as claimed in claim 3, wherein the nonaqueous organic solvent is in an amount of 0.5-100 g per gram of the 1-bicyclo[2.2.1]hept-5-en-2-ylmethanamine.

9. A process as claimed in claim 1, wherein the reacting is conducted at a temperature of −10 to 50° C.

10. A process for producing N-(bicyclo[2.2.1]hept-5-en-2-ylmethyl)-1,1,1-trifluoromethanesulfonamide represented by formula [3], comprising the sequential steps of:

charging a reactor with (i) 1-bicyclo[2.2.1]hept-5-en-2-ylmethanamine represented by formula [2], (ii) 0.2-100 g of water per gram of the 1-bicyclo[2.2.1]hept-5-en-2-ylmethanamine, (iii) 0.5-100 g of a nonaqueous organic solvent per gram of the 1-bicyclo[2.2.1]hept-5-en-2-ylmethanamine, and (iv) a base that is at least one selected from the group consisting of lithium hydroxide, sodium hydroxide, potassium hydroxide, magnesium hydroxide, calcium hydroxide, barium hydroxide, potassium carbonate, sodium carbonate, sodium hydrogencarbonate, sodium acetate, potassium acetate, disodium hydrogenphosphate, and dipotassium hydrogenphosphate; and intermittently or continuously introducing trifluoromethanesulfonic anhydride represented by formula [1] into the reactor at a temperature of −10 to 50° C., thereby reacting the trifluoromethanesulfonic anhydride with the 1-bicyclo[2.2.1]hept-5-en-2-ylmethanamine.

$(CF_3SO_2)_2O$     [1]

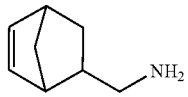
[2]

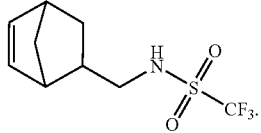
[3]

11. A process as claimed in claim 10, wherein the base is at least one selected from the group consisting of sodium carbonate, potassium carbonate, sodium hydroxide, and potassium hydroxide,
wherein the water is in an amount of 2-6 g per gram of the 1-bicyclo[2.2.1]hept-5-en-2-ylmethanamine, and
wherein the nonaqueous organic solvent is in an amount of 2-5 g per gram of the 1-bicyclo[2.2.1]hept-5-en-2-ylmethaneamine.

* * * * *